United States Patent [19]

Hammerstedt et al.

[11] Patent Number: 5,026,342

[45] Date of Patent: Jun. 25, 1991

[54] NONINGESTIBLE SEPARATION BARRIER WITH PLUGGED PORES

[75] Inventors: Roy H. Hammerstedt; Alec D. Keith, both of Boalsburg, Pa.; Rupert P. Amann, Fort Collins, Colo.

[73] Assignee: Biopore, Inc., Centre Hall, Pa.

[21] Appl. No.: 493,475

[22] Filed: Mar. 14, 1990

Related U.S. Application Data

[60] Division of Ser. No. 416,347, Oct. 6, 1989, which is a continuation-in-part of Ser. No. 263,049, Oct. 26, 1988, abandoned.

[51] Int. Cl.$^5$ .......................... A01N 1/02; C12N 11/04
[52] U.S. Cl. ........................................... 600/35; 435/2
[58] Field of Search ..................... 600/33–35; 435/2

[56] References Cited

U.S. PATENT DOCUMENTS 3,712,303  1/1977  Merkt et al. ........................... 600/35
4,840,891  6/1989  van Blerkom ..................... 600/35 X

*Primary Examiner*—Alan Cannon
*Attorney, Agent, or Firm*—Webb, Burden, Ziesenheim and Webb

[57] ABSTRACT

A noningestible separation barrier having one or more pores of micropores (of one or more diameters) therein, with the pores or micropores being initially plugged with one or more materials selected for its/their solubility and/or integrity characteristics relative to certain environmental conditions. Ordinarily, the pores or micropores of the noningestible separation barrier are initially filled with at least one material having greater erodibility, under a given environmental condition, than the material constituting the separation barrier itself. The combination of the release rate (if any) or other membrane characteristic of the separation barrier, combined with the release rate and/or erosion life of the plugged pores, enables complex separations including variable release of cells, colloids, solutes or solvents over time, such as when the plugged pores remain intact until erosion is triggered by an environmental change such as solvent addition or ionic conditions or pH or thermal change. Particular applications include specialized receptacles and protocols for the preservation of rooster sperm and turkey sperm for use in commercial artificial insemination applications.

9 Claims, 2 Drawing Sheets

NONINGESTIBLE SEPARATION BARRIER WITH PLUGGED PORES

This application is a continuation of application Ser. No. 7/416,347, filed Oct. 6, 1989, which is a Continuation-in-Part of U.S. patent application Ser. No. 07/263,049, filed Oct. 26, 1988, abandoned.

FIELD OF THE INVENTION

The invention relates to separation technology, including membranology and controlled release of solvents, solutes, or cells.

BACKGROUND OF THE INVENTION

Advances in the selective separation of matter have resulted in numerous developments in a wide variety of industries. Attention first centered on the science of membranology, beginning in about 1960, when integrally-skinned cellulose acetate hyperfiltration membranes were developed for hyperfiltration desalination of salt water. Developments followed in the areas of hemodialysis, electrodialysis, reverse osmosis, ultrafiltration, cell harvesting, membrane bioreactors, microfiltration, gas separation, controlled time release, gel permeation chromatography, hollow fiber technology, non-cellulosic polymer membranes, ionomer membranes, copolymer membranes, crosslinkable thermoplastic polymer membranes, emulsion-type liquid membranes and others. These innovations have gained general acceptance, and separation materials form the above disciplines are in widespread use in medical processes, pharmaceutical research and production, industrial processes, research tools and consumer products including consumer products packaging materials.

Controlled release of pharmaceuticals is now possible due to various technologies, which include application of slow-dissolving coatings to oral dosage form drugs. U.S. Pat. No. 4,755,180 discloses an oral drug dosage form in which an erodible material, formed as a film around the drug during manufacture, is eroded or leached from the wall of the dosage form, such erosion or leaching enabling controlled release of pharmaceutically active agents to the gastrointestinal environment. The erodible materials disclosed in U.S. Pat. No. 4,755,180 are typical of the polysaccharide (sugar) coatings common in such applications: poly(glycolic) or poly(lactic) acid compositions, gelatinous compositions, or leachable polysaccharides, salts or oxides. Enteric coatings are also known in the art, which do not dissolve in the stomach but allow enteric delivery of an orally dosed drug.

Although means are known for moving ions or molecules—or solvents—at simple rates, such as the "zero-order" or "first-order" release kinetics typical in controlled release pharmaceuticals, no technology has heretofore provided a noningestible means for complex separation technology in which the separation kinetics may change over time, in response to an environmental stimulus, in a pre-planned or pre-programmed manner; moving components into and out of a container to provide a better environment for the retained materials; or release of cells in a controlled manner. Accordingly, a need remains for a separation barrier which can provide complex separation protocols for particular separation applications entirely different from the oral pharmaceutical dosage forms.

SUMMARY OF THE INVENTION

In order to meet this need, the present invention is a noningestible separation barrier having one or more pores or micropores of one or more sizes therein, with the pores or micropores being initially plugged with a material selected for its solubility and/or integrity characteristics relative to certain environmental conditions. Ordinarily, the pores or micropores of the separation barrier are initially filled with at least one material having greater erodibility, under a given environmental condition, than the material constituting the separation barrier itself. Ordinarily, the separation barrier with its plugged pores is prepared prior to filling with the materials to be separated. The combination of the release rate (if any) or other membrane characteristic of the separation barrier, combined with the release rate and/or erosion life of the plugged pores, enables complex separations including variable release of cells, colloids, solutes or solvents over time, such as when the plugged pores remain intact until erosion is triggered by an environmental change such as solvent addition, pH, or thermal or radiation (ultraviolet light, etc.) change. Particular applications include specialized protocols for the preservation of rooster sperm and turkey sperm for use in commercial artificial insemination applications.

DETAILED DESCRIPTION OF THE INVENTION

Figure 1:
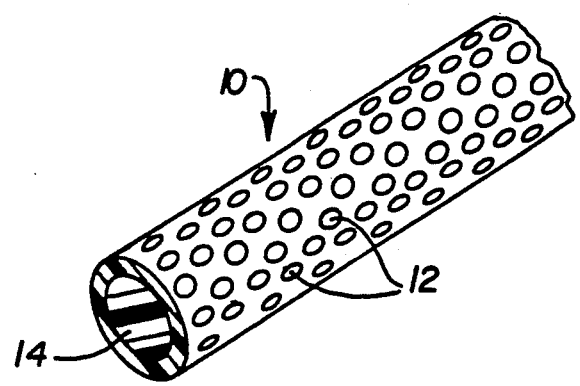
FIG. 1 is a hollow tubule (hollow fiber) separation barrier having plugged micropores.

The present invention is a noningestible separation barrier having one or more pores or micropores of one or more sizes therein, plugged with a material selected for its solubility or erodibility upon exposure to certain environmental conditions. The material forming the separation barrier itself may also have erodibility or solubility, as long as the separation barrier and plugged pores do not consist of the identical composition of matter. The combination of the release rate (if any) or other membrane characteristic of the separation barrier, combined with the release rate and/or erosion life or lives of the plugged pores, enables complex separations including variable release of cells, colloids, solutes or solvents over time.

Separation barriers having plugged pores, according to the present invention, have a wide variety of uses in a myriad of industries. Suitable applications include cell cultures and cryobiology, preingestion preservation and storage of food and pharmaceuticals, shelf-life extension of polymers, proteins and other products, and the containing, transporting and dispensing of active agents including cells, herbicides, pesticides, fertilizers, disinfectants, indoor air fresheners, and cell growth nutrients or other biologically active agents for use in laboratory or industrial settings.

Because the scope of the present invention is particularly broad, in view of the numerous variations in the product and process claimed as well as widespread applications thereof, a specific example is the best introductory illustration of the present separation barrier having initially plugged pores. For example, cryopreservaton of spermatozoa for artificial insemination, in certain species, has heretofore required process steps which can be eliminated by the complex separation protocols possible with the present invention. Ordinarily, cryopreservation of spermatozoa requires attention to three considerations. First, cryopreservation requires selection of an appropriate container, including appropriate volume, dimensions, material, thermal properties, etc., with the appropriate choices usually including nonporous glass ampules or vials, plastic vials or straws or metal tubes. Second, a cryoprotectant must be selected to ensure survival of the cells during cooling from 38° C. to 0°-5° C., subsequent cooling to minus 196° C., and subsequent rewarming above 0° C. Conventional cryoprotectants include egg yolk, lipoproteins, milk proteins, glycerol, dimethylsulfoxide, polyethylene glycol, sugar and others. Third, controlled post-thaw modification of the cellular and intracellular environment is essential for certain species. For example, rooster sperm must be serially diluted with a medium free from the cryoprotectant, followed by centrifugation and resuspension in the same cryoprotectant-free medium. This latter process, although cumbersome, has in the past been essential to avoid the inevitable contraceptive effect of the presence of the cryoprotectant around and within the sperm at the moment of artificial insemination.

As is explained in greater detail in Example 1, below, the present separation barrier having plugged pores simplifies thawing and removal of the cryoprotectant from the spermatozoa of the rooster. Referring now to FIG. 1, the terminal portion of a sealed polymeric tubule is illustrated, comprising the tubule 10 having plugged micropores 12 therein and an end seal 14. The end of the tubule not shown may comprise an open end; alternately, the seal 14 may be removed or originally omitted to leave an open end to the tubule 10. The tubule may be prelabelled for identification or may be adapted for insertion of a labelled plug in the open end. Collected rooster semen, evaluated, pooled, extended with media and processed by means known in the art, is cooled to 5° C., mixed with cryoprotectant (if cryoprotectant is absent from the original extension media), and charged to the interior of the tubule 10 of FIG. 1. The tubule 10, a polymeric barrier having polymer-plugged micropores 12, constitutes the storage container for cryopreservation of the rooster semen. The open end of the tubule is then sealed. The sealed tubule and its contents are then cooled at one or more controlled rates, as known in the art, to −196° C.

Prior to insemination of a group of chickens, a tubule 10 is transferred from cryopreservation storage at minus 196° C. (liquid nitrogen) into a thawing solution known in the art, and after initial thawing the tubule 10 is subsequently transferred to a post-thaw treatment solution of appropriate temperature, composition and oxygenation. In the post-thaw treatment solution, the action of at least one of the constituents of the post-thaw treatment solution on the plugged micropores 12 opens the micropores 12 and allows controlled egress of the cryoprotectant from the environment around and within the rooster sperm and simultaneously permits controlled ingress of the post-thaw treatment solution into the tubule 10. The micropores 12 are, of course, smaller than the sperm cells. After a 10–60 minute treatment period, sperm in the tubule are ready for use. The tubule 10 may be used, along with appropriate auxiliary mechanical devices, to disperse the sperm directly into one or more hens for artificial insemination of the chicken flock, or the sperm may be transferred from the tube into an appropriate auxiliary mechanical device for insemination. As an illustration of the concept of the present invention, the tubule 10 is insoluble in the liquid nitrogen at minus 196° C., as are the polymer plugged micropores 12. Both the tubule 10 and plugged micropores 12 are likewise insoluble or not completely eroded in t he thawing solutions known in the art. Thus, during two periods of use, the tubule 10 undergoes no separation or change in separation kinetics with respect to its contents or structure. However, upon contact with the post-thaw treatment solution, the action of at least one constituent of the post-thaw treatment solution constitutes the environmental factor which commences or completes dissolution of a selected polymer within the plugged micropores 12, so that pre-determined time- and rate-controlled egress of cryoprotectant and ingress of medium is accomplished. If two or more cryoprotectants are used, they can be removed selectively through pores having different sizes and/or erosion characteristics (as suggested in FIGS. 2 and 3).

It will be understood by those skilled in the art that both the plugged micropores 12 and the tubule 10 (the separation barrier itself) may both be fabricated of materials soluble or erodible under certain conditions. For example, the plugged micropores 12 may be moderately soluble in human plasma, with the tubule 10 being only somewhat soluble in human plasma, so that an entire structure comprising a small tubule 10 according to FIG. 1, filled with a pharmaceutically active agent, would constitute a human subcutaneous controlled release drug implant which would not release the agent for some period of time, then release the agent at a controlled rate, and ultimately completely erode. Likewise, tubules 10 according to FIG. 1, or other structures such as that shown in FIG. 3, may be used in the cryopreservation of a wide variety of cells and cell cultures, with the polymer or other material for plugging the plugged micropore 12 being selected in reliance on the reaction or release kinetics required by the particular post-thawing parameters required for the preserved cells. Additional applications include controlled release of nutrients to cells or organisms; bacteria; herbicides; and release of alkaline agents to neutralize water or soil, each triggered by the appropriate change in environmental conditions.

Separation barriers according to the present invention may be fabricated from a wide variety of materials including polymers, ceramics, metals and natural and semi-synthetic cellulosics. More particularly, the separation barrier may consist of a wide variety of materials and polymers including polyether compositions, polyethylene and polypropylene polymers, polyvinyl polymers, moisture vapor permeable urethanes and other polyurethanes, polycarbonate polymers, cellulosics, semi-synthetic cellulosics, ceramics, metals, natural resins including rubbers, etc. When appropriate, the separation barrier may be fabricated of one or more of the compositions also suitable for use in plugging the pores or micropores in the separation barrier, which compositions include cellulosics (i.e., hydroxypropylmethylcellulose), polyelectrolyte complexes, polysulfone compositions, acrylic polymers, cellulose acetates, Dynel ® compositions, polyacrylonitrile compositions, polyvinylpyrrolidone polymers, cellulosic composites on polyvinyl chloride, and other materials known in the membranologic arts. Also feasible are selectively soluble salt or polysaccharide crystals as long as the dissolution of same does not poison adjacent biologic media and is not toxic to cells in or near the barrier. Selection of one or more materials for the preparation of the separation barrier having plugged pores will be dictated directly by the specific application intended and the release kinetics desired. Also, the separation barrier may be constructed for one-time use, or may be designed for multiple uses i.e., when the barrier device is returned to the producer for replugging and refilling.

As an overview of the various applications of the different types of "plugger" polymers, water-soluble materials included within the pores or micropores of the separation barrier will have applicability at least to cryobiologic preservation of spermatozoa (poultry, human, horse, fish, pig, sheep, dog, mouse, rat, etc.); oocytes (cattle, human, horse, pig, mouse, rat, etc.); embryos (human, cattle horse, mice, dogs, etc.) of all species of mammals with physiological need and economic advantage; human pancreas B-cells; human corneas; primary cell cultures; and seeds. Controlled release of animal agricultural hormones; plant agricultural fertilizers, herbicides, and pesticides; seeds; agriculture nutrients, pharmaceuticals and larvae; and home insecticides, fertilizers and herbicides is also envisioned. Thermal sensitive polymer plugs have application in frost damage control: erodibility of the plugs, in the separation barrier pores, can upon decreasing temperature release frost-protective bacteria onto crops, fields or orchards. Polymer plugs having pH sensitivity may be applied to the non-oral controlled release of pharmaceuticals to animals and humans in pH-fluctuating anatomic areas, and likewise have application in the ecosystem to deliver the appropriate acid or base upon a drop or increase in environmental pH conditions. Photoinducible polymer erodibility can release agricultural materials after sufficient exposure to sunlight. Other environmental conditions including electricity, sound and magnetism can also be harnessed by appropriate "plugger" material types, which erode at the appropriate cued time. Finally, environmental cues can trigger polymerization, instead of erosion, of the material in the pores or micropores. Other examples will be readily evident to those skilled in the art.

Figure 2:
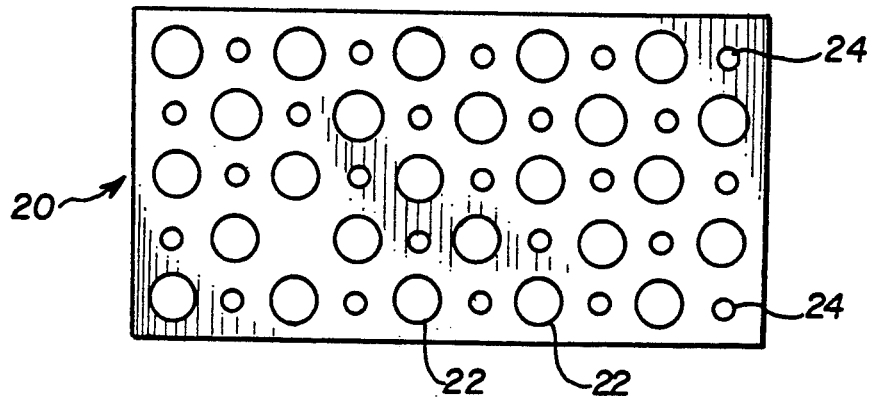
FIG. 2 is a side elevational view of a separation barrier membrane having small and large pores plugged with two different polymers, respectively.

Referring now to FIG. 2, a side elevational view of a membrane 20 is shown having pores of two different diameters. The large pores 22 are filled with a first polymer composition and the small pores 24 are filled with a second and different polymer composition. By appropriate selection of the material constituting the membrane 20 and the material within each of the large pores 22 and the small pores 24, any one of three or all three separation kinetics attributable to the respective polymers may be controlled by appropriate changes in the corollary environmental conditions including temperature, pH, presence of specific solvents, electrical charge, magnetic field, light waves, or sound energy. For example, if the largest pores open last, the largest separable particles cordoned by the membrane will diffuse last. The membrane 20 of FIG. 2 may be used in lieu of other prior art separation membranes, when the sequential or selective separation kinetics possible with the membrane 20 are desired or necessary for a given application. Such a membrane can be directly fabricated into a variety of shapes, or used as a sheet for later insertion into an appropriate container.

Figure 3:
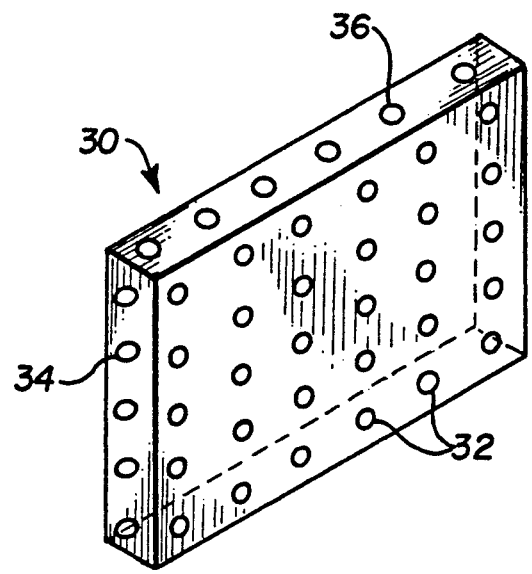
FIG. 3 illustrates a three-dimensional rectangular construct, closed on five sides, having plugged micropores on each closed polymer face thereof, with the pores in each closed polymer face being plugged with materials having different erosion characteristics.

FIG. 3 illustrates a three-dimensional rectangular construct having five closed sides, or faces. The rectangular construct 30 is fabricated of a polymer, and the largest closed face thereof has polymer-plugged pores 32 therein. The remaining closed faces shown have polymer-plugged pores 34 and 36 therein. Polymer plugged pores 32, 34, and 36 are filled with a second, third, and fourth polymer, respectively. As with the device shown in FIG. 2, the rectangular construct 30 functions as building-block type unit, and can be used alone or in an array of a number of identical rectangular constructs 30 for laboratory or production use in a variety of configurations. Complex sequential or selective separations are possible due to the varied polymer plugs in the polymer-plugged pores 32, 34, and 36. The remaining closed faces not shown may also contain plugged pores. The rectangular construct 30 is representative of a commercial embodiment of the present separation barrier having plugged pores, in which units may be assembled by the user as needed.

Referring once again to the present separation barrier generally, the plugged pores may be true plugged pores, i.e., the pores in the separation barrier may be filled to the extent of the pore cavity only, or the plugged pores may be plugged by means of a continuous coating on one or both sides of the separation barrier to plug the pores by coating over them. Also, with respect to either the separation barrier itself or the pore-plugging material, or both, additional treating materials may be used to alter the chemical and physical properties of the polymers, such as for altering toxicity, adapting polar and non-polar materials for their specific intended applications, or increasing bonding properties.

Although the structures represented in FIGS. 1-3 are illustrative, numerous other containers may be fashioned in view of the concept of the invention. A container need not be homogeneous, for example, but could have sides each of different materials. A six-sided construct could include six different materials in the different-sized pores of each respective side, for example, which construct would then effect unique separation kinetics by means of each of its separate sides.

Dimensions for the tubule of FIG. 1, for cryopreservation of sperm, range from 1-80 mm. in diameter or more, with 1-5 mm. diameters being preferred. The tubules may range in length from about 5 mm. to 10 centimeters or more, with about 50-200 mm. being preferred. Pores or micropores may be of any size. For many separations, pores of 0.2 to 0.6 micrometers effective diameter are preferred, but for some applications only pores greater than 0.6 micrometers are appropriate. Often pores can be larger than the pores in prior art separation membranes due to the nature of the materials to be retained and the initial plugged configuration of the pores. Other embodiments of the invention may have widely varied dimensions depending upon the intended application.

Polymers which can provide a persistent plug in a number of environments include ethyl cellulose, among others. For applications requiring water erodible plugs, methyl cellulose plugs are appropriate. The use of polyvinylpyrrolidone enables thermal transition opening of the pores containing it, and carboxymethylcellulose allows pores to open in response to pH shift. Detergent activated, photoactivatable, and other compositions known in the art can be selected as needed.

A further particular application of the present invention is in the production of fertilized turkey eggs, which eggs can be produced commercially only by artificial insemination (AI). Prior art methods permit commercial holding of turkey sperm for only six to eight hours after collection, which allows only about two hours for transport of the turkey sperm. In the laboratory, oxygenation of turkey sperm has increasing the holding time to about 24 hours, but the laboratory techniques have been impractical on a commercial basis. By applying the products and methods according to the present invention, turkey sperm viability and quality should be maintained for up to 48 hours. Preservation of turkey sperm is discussed further below and in Example IV herewith.

The present invention provides for the use of unique containers and storage conditions for preservation of turkey sperm. The container is uniquely constructed with pores that are ordinarily initially impermeable (allowing easy loading and handling) but which open rapidly after the container of turkey semen is placed in contact with exchange solutions. Precise control of temperature and oxygen content and continuous exchange of nutrients and antioxidants into the sperm suspension, without damage to the sperm, is possible using the container along with an optional microprocessor controlled system. This will allow the industry to create "super stud farms" with the potential for total reorganization of the distribution of germ plasm.

Despite current limitations of semen holding/storage, the industry exists only because of use of AI for reproduction. Passage from the breeder to the commercial producers is by sale of eggs of the individual male and female lines as needed for the construction of the commercial genetic product. If held or stored semen were available, industry needs could be better satisfied and several problems would be eliminated. First, geographical separation of males and females is desirable to allow optimum management of each. Increasing the holding time makes possible wider use of stud farms. Second, coordinating purchase of male line with female eggs to meet future needs is difficult. Shortages of one line are costly. Held semen would alleviate this problem. Third, selection for production traits of individual males could be increased, thus decreasing the cost per pound of meat to the consumer. Fourth, purchase of semen instead of eggs removes the cost and nuisance of offsex disposal. Fifth, the breeder will have greater control over the quality of the commercial meat bird, again to the benefit of the consumer. Finally, the breeder will have greater protection of the male line germ plasm.

The general approach to preservation of turkey sperm is as follows. Turkey toms (e.g., male line meat strain) are ordinarily housed in a room with 14:10 hour light:dark cycle. Semen is collected by massage every 3-4 days from a group of toms and pooled within a few minutes. Sperm quality is determined by several tests, as are known to the art. Several extenders have been developed for holding turkey sperm and 5° C. and are known in the art, and these extenders may be admixed with acceptable turkey semen and placed within plugged-porous containers according to the present invention.

The appropriate plugged porous container is ordinarily fabricated from nylon "frames" and specially prepared polysulfone membranes with 0.22 $\mu$m pores, with the pores initially sealed using methyl cellulose and ethyl cellulose. Identical membranes are fastened to both large faces of the container using IV-activated glue. These containers are nontoxic to turkey sperm and have pores that open in a controlled and repeatable manner. Transmembrane flux of small molecules (<10,000 kD) in the internal or external diluent has a half-time of about 2-5 min.; sperm cannot pass through the membrane. The above-identified polymers are exemplary.

The containers are incubated in special environmental control units. Chambers are fabricated and fitted with circulation pumps, miniature oxygen sensors, small air pumps, electronically controlled air nitrogen valves, and a small oxygenation reservoir. The total volume of the chamber is about 30 ml; the chamber is preferably fitted with control circuits. Alternatively, the desired oxygen content in the medium can be achieved using appropriately blended gas mixtures and a constant rate of addition with a diffuser, as are known in the art. When the containers (containing suitable diluents and extenders along with the turkey semen) are cooled and held within the appropriate exchange solutions in the controlled chamber, turkey sperm viability and quality can be maintained for >18, and possibly >48, hours.

Although the use of a porous container held within a chamber containing dialyzing fluid is novel, the appropriate extenders, diluents and exchange solutions are known in the art. The environmental control chamber regulates oxygen tension and temperature of turkey sperm to which have been added diluents and/or extenders; the present invention provides the heretofore unknown means by which cooling, selective oxygenation, antioxidant treatment, etc., of turkey sperm may be scaled up to a commercially feasible level using porous containers. A particularly noteworthy aspect of the cooling/selective oxygenation preservation of turkey sperm is the option whereby extended and/or diluted turkey semen may be charged to a porous container in which the pores are not initially plugged, simultaneous with immersion of the porous container in the exchange solution. (The pores have a diameter smaller than the diameter of the turkey sperm cells, of course.)

Figure 4:
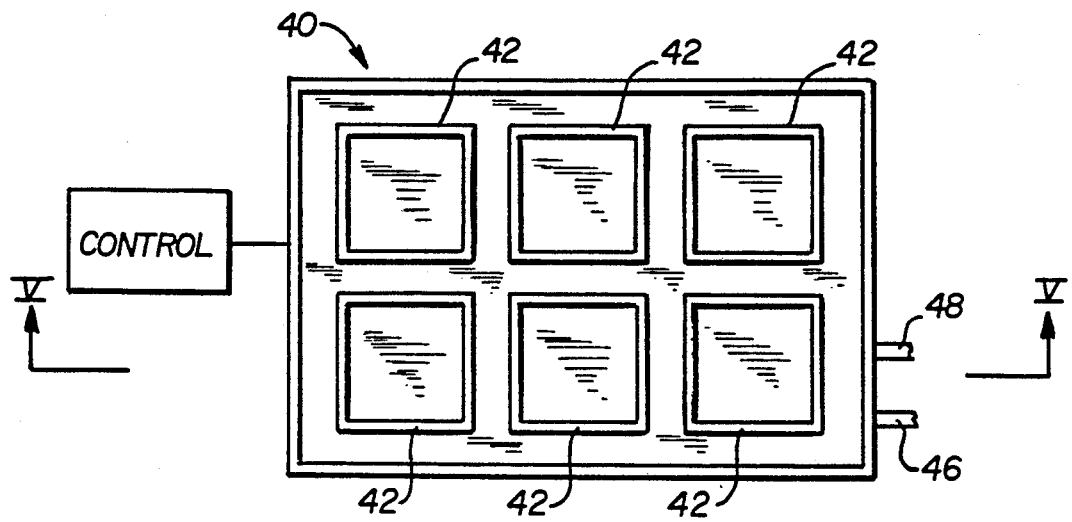
FIG. 4 is a schematic illustration (plan view) of a chamber which contains exchange medium and into which are placed six containers according to the present invention.
Figure 5:
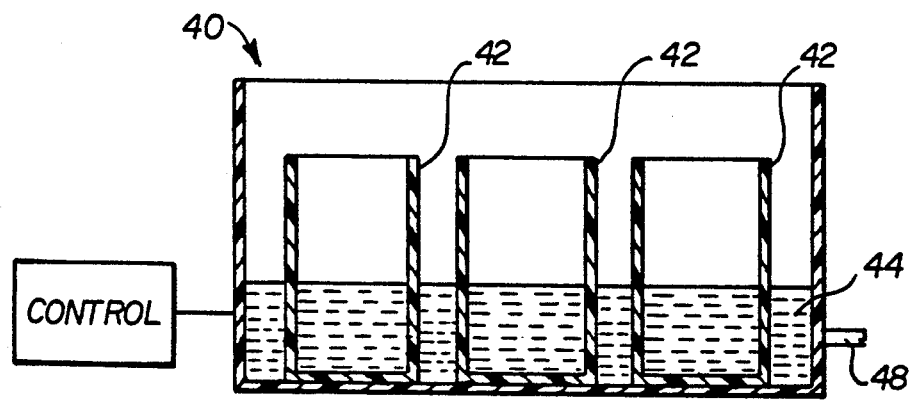
FIG. 5 is a section taken along lines V—V of FIG. 4.

Referring now to FIGS. 4 and 5, an apparatus suitable for preservation of turkey semen is illustrated schematically in plan and sectional views, respectively. A five-walled chamber 40 has control means for controlling temperature and oxygenation (for example, oxygen concentration can be monitored with a miniature oxygen sensor connected to a multiplex A/D converter, with optional electronic data storage) and acts as a bath-type receptacle for turkey semen receiving containers 42. Exchange fluid 44 selectively enters and exits the chamber 40 via inlet 46 and outlet 48 as desired, and the exchange fluid 44 can enter and exit the containers 42 depending upon the constituents of the fluid and the pore size of the container(s).

The invention will be more particularly described by means of the following illustrative examples.

EXAMPLE I

Frozen rooster semen is not successfully used commercially because the cryoprotectant most effective for spermatozoa survival during freezing and thawing, glycerol, also demonstrates contraceptive properties after artificial insemination. By prior art methods this cryoprotectant is removed by serial dilution followed by centrifugation or conventional dialysis. Such processes successfully reduce cryoprotectant concentration but are commercially impractical.

Because of the contraceptive effect of the glycerol, therefore, the glycerol must be removed from the avian spermatozoa prior to artificial insemination. However, rapid removal of glycerol from avian spermatozoa damages the spermatozoa cells, probably as a consequence of rapid movement of glycerol across the cell membrane, which alters the characteristics of the membrane and the viability of the cell. Slow removal of glycerol from cryopreserved rooster semen is therefore a necessity, notwithstanding the typical high cost of achieving it according to prior art techniques.

Use of the present separation barrier having plugged pores, for the controlled removal of cryoprotectant from rooster spermatozoa, is described below.

A group of roosters raised by an integrated breeder is selected, which roosters possess a virtually identical genetic background and therefore transmit the same phenotype. Semen is collected from this group of roosters, a collection unit, with the semen then being evaluated, pooled, extended, and cooled by means known in the art. (Oxygenation is required if the cells are held above 15° C. because avian spermatozoa are highly dependent on oxidative metabolism unless they are cooled to near 5° C. or frozen.) Initial cooling proceeds to 5° C. After the extended semen achieves 5° C., glycerol is added as a cryoprotectant (if not present in the original extender), and the cryoprotected extended semen then is immediately charged to hollow tubules having plugged micropores such as the tubule illustrated in FIG. 1.

More particularly, the hollow tubule is a cylindrical polymeric separation barrier open at one end and having plugged pores therein, having the following features: (1) impermeable for 20-30 minutes to aqueous solutions placed inside at 5° C.; 2) impermeable to viruses or bacteria coming in contact with the outside of the tubule, while the pores remain plugged; (3) resistant to immersion and long-term storage in liquid nitrogen; (4) resistant for 6-300 seconds to warming in aqueous solutions at 2°-75° C.; (5) has pores partially soluble upon 5-20 minutes' further immersion in aqueous post-thaw treatment solutions at 5°-38° C.; and 6) develops pores of a size which permit only molecules below a certain size to pass. These features are accomplished by means of a microporous hollow fiber having the following characteristics; (1) wall thickness, 0.5 mm; length, 60 mm.; and diameter, 4 mm. (other possible configurations include: a right cylinder (30-40 mm. diameter and 5-10 mm. in length) of a nonporous material, such as polystyrene, to which is attached a "lid" of the microporous membrane described herein, or a flattened tube 2 mm.×20 mm.×60 mm.); (2) separation barrier constructed of polyethylene (or other acceptable polymer); and (3) 0.2 micrometer micropores plugged with methyl cellulose.

If a three-dimensional rectangular device is used, to provide greater capacity or an alternative packaging process, it would have five impermeable sides, fabricated from polystyrene or another material, forming a square or rectangular shape (25 mm,×25-40 mm.×5-10 mm.) and the sixth surface would be a microporous membrane with plugged pores, applied and sealed as a lid.

Cryopreservation of the semen in the hollow tubules (or tubes or other containers described above) is effected by means known in the art. Shortly before insemination of a flock of chickens, a tubule is removed from liquid nitrogen in storage at minus 196° C. and is transferred to a thawing solution. After thawing, the hollow tubule is transferred to an aqueous post-thaw treatment solution including additives necessary for the optimal survival of the avian spermatozoa (with oxygenation, if appropriate). Upon immersion in the post-thaw treatment solution, the plugged pores open to permit controlled and relatively slow egress of glycerol cryoprotectant from the solution within the container, and hence from the spermatozoa, and simultaneous controlled ingress of the external medium to surround the thawed rooster sperm. The thawed and treated rooster sperm then are ready for use in artificial insemination.

EXAMPLE II

A second example is provided to illustrate the concept of two different rates of release, as well as an extended time for initiation of pore opening.

For human sperm, both glycerol and crude lipid micelles (e.g., egg yolk lipoprotein particles) are used in the art of cryopreservation. It is desirable, after thawing, to remove the glycerol slowly (as for rooster sperm) and then rapidly remove the egg yolk lipoprotein particles. To accomplish this objective, the general process of Example I is followed except that the initial extender contains egg yolk and is centrifuged (20,000×g for 30 minutes, for example) or filtered (through a 0.2 or 0.4 micrometer filter) to remove material larger than the dimension desired for the colloidal particles, and glycerol is added after the extended sperm are cooled to 5° C.

The container is a three dimensional rectangular construct (although the shape is not important) with four nonporous sides. One of the other sides is a microporous membrane with pores (about 0.2 micrometers diameter) plugged with a material (i.e., high ratio of methyl cellulose to ethyl cellulose) having erodibility characteristics suitable for the controlled removal of glycerol. These pores open soon after immersion of the container into the thawing solution. The last face consists of a microporous membrane with different size pores (0.3-0.5 micrometers) plugged with a different material (i.e., low ratio of methyl cellulose to ethyl cellulose) that is rapidly eroded after a time delay (30-40 minutes) to allow rapid egress of the egg yolk lipoproteins and further entrance of the treatment medium.

EXAMPLE III

A third example is provided to illustrate release of soluble materials to the environment and an alternative mode of release in response to changing environmental conditions.

Nutrients may be provided to cultured cells held within "bioreactors". Continuous culture of cells for purpose of production of pharmaceuticals and other bioproducts requires (at a minimum): removal of the desired products as they are excreted into the growth medium; removal of toxic side products from the medium; and selective means for replenishing nutrients and regulatory substances necessary for continued culture of the cells.

Controlled release of nutrients and regulatory substances is achieved by the following process. A hollow tube, composed of one or more pores plugged with one or more materials chosen to allow selective opening under environmental stimulus, is filled with a sterile suspension (solid or liquid) or solution of the materials needed for continuous growth and production by the specific cells under culture. Examples include vitamins, hormones, trace metals, etc. The surface of the tube then is sterilized, yielding a container that allows long thermal storage of the materials to be added to the culture, and facile insertion into the bioreactor network as needed.

The tube is inserted into the culture (directly or into circulating media) as needed. In response to this new environment, the pores open to release the materials to the cells. The environmental signal is either a passive (water based erosion of the pore plug, as outlined for the treatment of rooster sperm) or an active response to the changing culture conditions (pH shift as induced by production of acid by-products (e.g., lactic acid) by the cells). Such a container can also be used in a large scale agriculture environment, i.e., addition of nutrients for growth of fish on a commercial scale.

Note: We have never done all the parts of this example.

EXAMPLE IV

A plastic chamber holds six rectangular plugged-pore containers plug exchange solutions. The chamber is fitted with control circuits, an "oxystat," a control means which enables maintenance of constant $O_2$ tension by way of differential addition of air or $N_2$, and with means known in the art for temperature control, pumping and valving.

Turkey semen is collected, pooled and extended by means known in the art; the extended turkey sperm is cooled at a linear rate to temperatures between 5° C. and 20° C. and $\geq 1.5$ ml aliquots are charged to each of the six rectangular plugged-pore containers. The containers have inside dimensions of 3.5×17×36 millimeters, although container having inside diameters of 3.0×17×22 millimeters could be substituted. The two largest walls of the containers are constructed of polysulfone membranes having 0.22 micrometer pores, with the pores initially sealed with methyl cellulose and ethyl cellulose. The containers are placed in the chamber containing exchange fluid at the desired temperature (5°-20° C.); the pores of the containers are no longer plugged after several minutes. Cooling and dialysis can continue for the holding period.

Although the invention has been described particularly above, the invention is only to be limited insofar as is set forth in the accompanying claims.

We claim:

1. A method for separating a mixture including spermatozoa and glycerol comprising:
   (a) selecting a noningestible barrier material suitable for containing said mixture;
   (b) providing at least one pore to said barrier material, which pore is small enough to prevent passage of at least one of the said spermatozoa or glycerol;
   (c) plugging said pore, with a material responsive to an environmental stimulus, to yield a plugged pore and a plugged barrier;
   (d) isolating together said mixture by means of said plugged barrier; and
   (e) exposing said plugged barrier at a preselected time to the environmental stimulus to which said plug in said pore is responsive.

2. A method for separating glycerol from frozen rooster sperm, comprising:
   (a) selecting a cylindrical polymeric separation barrier open at one end and having plugged pores therein, wherein said plugged pores incorporate a methyl cellulose composition, wherein said plugged pores are impermeable for at least 20 minutes to aqueous solutions at 5° C., wherein said plugged pores are impermeable to viruses and resistant to long-term storage in liquid nitrogen, wherein said plugged pores are further resistant to warming in aqueous solutions and temperatures of 2°-75° C. for 6-300 seconds, and wherein said plugged pores are at least partially soluble in one or more aqueous post-thaw treatment solutions at a temperature of between about 5°-38° C., and further wherein said cylindrical polymeric separation barrier has a wall thickness of about 0.5 millimeters, a length of about 60 millimeters and a diameter of about 4 millimeters, and further wherein said cylindrical polymeric separation barrier is constructed of polyethylene;
   (b) collecting rooster semen and evaluating, pooling, extending and cooling it;
   (c) charging the evaluated, pooled, extended and cooled rooster semen to said cylindrical polymeric separation barrier, sealing the open end, and storing said cylindrical polymeric separation barrier in liquid nitrogen at $-196°$ C.;
   (d) thawing aid cylindrical polymeric separation barrier in a thawing solution;
   (e) transferring said cylindrical polymeric separation barrier from said thawing solution to an aqueous post-thaw treatment solution;
   (f) maintaining said cylindrical polymeric separation barrier in said aqueous post-thaw treatment solution for an amount of time effective to permit controlled and relatively slow egress of glycerol cryoprotectant from within said cylindrical polymeric separation barrier, with simultaneous controlled ingress of the aqueous post-thaw treatment solution into the thawed rooster sperm; and
   (g) using the rooster sperm as prepared in steps (a) through (f) above in the artificial insemination of chickens.

3. A method for preserving turkey semen, comprising:
   (a) collecting turkey semen, and adding an optional diluent or optional extender;
   (b) charging a quantity of said turkey semen into a receptacle having at least one plugged pore therein and further having an access means thereto other than said plugged pore; and
   (c) controlling the temperature and oxygenation of said turkey semen throughout a period of storage of said turkey semen.

4. The method according to claim 3, wherein step (b) further comprises the step of:
   (b) charging a quantity of said turkey semen into a receptacle having at least one pore therein, said pore being plugged at the time of the charging of the turkey semen with an erodible composition;

5. The method according to claim 3, wherein step (b) further comprises the step of:
   (b) charging a quantity of said turkey semen into a receptacle having at least one micropore therein, said micropore being plugged at the time of the charging of the turkey semen with one or more cellulosic compositions.

6. The method according to claim 5, wherein said micropore has a diameter of 0.22 micrometers.

7. The method according to claim 5, wherein step (c) further comprises the step of:
(c) controlling the temperature and oxygenation of said turkey semen by bathing said receptacle in a chamber equipped with control means therefor and containing exchange fluid therein.

8. The method according to claim 7, wherein each of said receptacle and said chamber is rectangular.

9. A method for preserving and separating a mixture of two or more materials including semen and an optionally added diluent or extender comprising:
(a) collecting semen and adding an optional diluent or an optional extender thereto to form said mixture;
(b) selecting a receptacle having at least one plugged pore therein and further having an access means thereto other than said plugged pore;
(c) charging a quantity of said mixture into said receptacle;
(d) controlling the temperature of the mixture throughout a period of storage of said mixture;
(e) removing said receptacle from the temperature controlled storage;
(f) transferring said receptacle to a post-storage treatment solution; and
(g) maintaining said receptacle in said treatment solution for an amount of time effective to permit controlled and relatively slow egress of said optional diluent or extender from within said receptacle, with simultaneous controlled ingress of the post-storage treatment solution into the semen.

* * * * *

UNITED STATES PATENT AND TRADEMARK OFFICE
CERTIFICATE OF CORRECTION

PATENT NO. : 5,026,342
DATED : June 25, 1991
INVENTOR(S) : Roy H. Hammerstedt, Alec D. Keith and Rupert P. Amann It is certified that error appears in the above-identified patent and that said Letters Patent is hereby corrected as shown below:

Abstract Line 2 "of" (1st occ.) should read --or--. (1st occ.)

Column 1 Line 31 "form" should read --from--.

Column 4 Line 18 "t he" should read --the--. (1st occ.)

Column 7 Line 13 "increasing" should read --increased--.

Column 9 Line 51 "characteristics;" should read --characteristics:--.

Column 11 Line 8 "thermal" should read --term--.

Column 11 Line 40 "container" should read --containers--.

Claim 2 d) Line 31 Column 12 "aid" should read --said--.

Claim 4 Line 63 Column 12 "composition;" should read --composition;.--.

Claim 5 Line 2 Column 13 "compositions." should read --composition;.--.

Signed and Sealed this

First Day of December, 1992

*Attest:*

DOUGLAS B. COMER

*Attesting Officer*   *Acting Commissioner of Patents and Trademarks*